United States Patent
Gore (10) Patent No.: US 8,474,954 B2
(45) Date of Patent: Jul. 2, 2013

(54) SYSTEM AND A METHOD FOR PHARMACEUTICAL DOSAGE PREPARATION USING JETTABLE MICROEMULSIONS

(75) Inventor: Makarand Gore, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 13/037,101

(22) Filed: Feb. 28, 2011

(65) Prior Publication Data

US 2011/0151103 A1   Jun. 23, 2011

Related U.S. Application Data

(62) Division of application No. 10/827,485, filed on Apr. 19, 2004, now abandoned.

(51) Int. Cl.
*A61K 47/00* (2006.01)
(52) U.S. Cl.
USPC .......................................... 347/84; 424/439
(58) Field of Classification Search
None
See application file for complete search history.

(56) References Cited

U.S. PATENT DOCUMENTS

| 6,623,765 | B1 * | 9/2003 | Dennis et al. | 424/502 |
| 7,727,576 | B2 * | 6/2010 | Figueroa et al. | 427/2.14 |
| 2002/0143072 | A1 * | 10/2002 | Aust | 516/98 |

OTHER PUBLICATIONS

Three Dimensional Printing, What is the 3DP Process?, Jun. 28, 2000.*
Bagwe et al. Improved Drug Delivery Using Microemulsions: Rationale, Recent Progress, and New Horizons, Critical Reviews in Therapeutic Drug Carrier Systems, 18(1):77-140 (2001).*
Three dimnesional Printing, What is the 3DP Process? Jun. 28, 2000.*
Three Dimensional Printing, Medical Applications: Drug Delivery Devices, Jun. 28, 2000.*
Bagwe et al. Improved Drug Delivery Using Microemulsions: Rationale, Recent Progress, and New Horizons, Critical Reviews in Therapeutic Drug Carrier Systems, 18(1 ):77-140 (2001).*
Woo, George, Formulation and Physicochemical Properties of macro- and micro emulsions prepared by interfacial ion-pair formation between, 1987.*

* cited by examiner

*Primary Examiner* — Robert A Wax
*Assistant Examiner* — Melissa Mercier (57) ABSTRACT

A jettable solution includes an oil, the oil being one of a naturally occurring oil, an edible oil, or a removable oil, an edible surfactant, an edible aqueous solution, and a pharmaceutical solubilized into the naturally occurring oil, in which the naturally occurring oil, the pharmaceutical, the surfactant, and the aqueous solution form a microemulsion.

10 Claims, 6 Drawing Sheets

SYSTEM AND A METHOD FOR PHARMACEUTICAL DOSAGE PREPARATION USING JETTABLE MICROEMULSIONS

The present application is a divisional application and claims the priority under 35 U.S.C. §120 of previous U.S. patent application Ser. No. 10/827,485 filed Apr. 19, 2004 now abandoned by Makarand Gore for "A System and a Method for Pharmaceutical Dosage Preparation Using Jettable Microemulsions."

BACKGROUND

Traditional oral dosage drug formulations include both active pharmaceutical ingredients (API) and inactive ingredients. The inactive ingredients, also called excipients, are components of the final formulation of a drug that are not considered active pharmaceutical ingredients (API) in that they do not directly affect the consumer in the desired medicinal manner.

Traditional oral dosage forms have several inactive ingredients. Among the traditional inactive ingredients included in oral dosage forms are binders that hold the tablet together, coatings configured to mask an unpleasant taste, disintegrants configured to make the tablet break apart when consumed, enteric coatings, fillers that assure sufficient material is available to properly fill a dosage form, enhancers configured to increase stability of the active ingredients, preservatives aimed at preventing microbial growth, and the like.

Traditionally, the formation of an oral dose drug often included combining a desired pharmaceutical product with a number of the above-mentioned materials designed to control the release rate of the API when consumed. While the traditional method is effective for a number of soluble drugs, there are a number of highly water insoluble drugs that are not well suited to sustained or controlled delivery. The formulation of these highly water insoluble APIs into controlled or modified-release dosage forms using traditional formulation methods is both expensive and challenging due to the APIs insolubility and unknown stability.

Microemulsion formulations potentially offer a variety of desirable properties for pharmaceutical delivery, namely, high solubility, high absorption, and improved pharmacokinetics. However, precise dispensing and distribution of the microemulsions formed for pharmaceutical product delivery has proven to be somewhat problematic as noted in the following publications: Using microemulsions for drug delivery, Pharmaceutical Technology, 1987; Improved drug delivery using microemulsions: Rationale, recent progress, and new horizons, Critical Reviews in Therapeutic Drug Carrier Systems, 2001; and Microemulsions: an overview and pharmaceutical applications, Critical Reviews in Therapeutic Drug Carrier Systems, 1999.

SUMMARY

A jettable solution includes a naturally occurring, edible, or removable oil, an edible surfactant, an edible aqueous solution, and a pharmaceutical solubilized into the naturally occurring oil, wherein the oil, the pharmaceutical, the surfactant, and the aqueous solution form a microemulsion.

BRIEF DESCRIPTION OF THE DRAWINGS

The accompanying drawings illustrate various embodiments of the present system and method and are a part of the specification. The illustrated embodiments are merely examples of the present system and method and do not limit the scope thereof.

Throughout the drawings, identical reference numbers designate similar, but not necessarily identical, elements.

DETAILED DESCRIPTION

A number of exemplary systems and methods for producing an ink jettable pharmaceutical based microemulsion are disclosed herein. More specifically, a jettable pharmaceutical based microemulsion is disclosed that may contain a number of water-immiscible pharmaceuticals. Moreover, an exemplary method for forming and dispensing the ink jettable pharmaceutical based microemulsion to form an oral dosage form is disclosed herein.

As used in the present specification and the appended claim, the term "edible" is meant to be understood broadly as any composition that is suitable for human consumption and is non-toxic. Similarly, the phrase "suitable for human consumption" is meant to be understood as any substance that complies with applicable standards such as food, drug, and cosmetic (FD&C) regulations in the United States and/or Eurocontrol experimental centre (E.E.C.) standards in the European Union. Additionally, the term "ink" is meant to be understood broadly as meaning any jettable fluid configured to be selectively emitted from an inkjet dispenser, regardless of whether the jettable fluid contains a pharmaceutically active ingredient or an oil containing solubilized pharmaceutically active ingredient. The term "jettable" is meant to be understood both in the present specification and in the appended claims as any material that has properties sufficient to allow the material to be selectively deposited by any digitally addressable inkjet material dispenser.

Additionally, in the present specification and in the appended claims, the term "amphiphile" or "hydrotrope" is meant to be understood as relating to, or being a compound such as a surfactant that includes molecules having a polar "hydrophilic" group attached to a hydrophobic hydrocarbon chain or cluster. Consequently, an amphiphile may include any of many organic compounds such as a surfactant, a detergent, a bile salt, or a phospholipid that is composed of hydrophilic and hydrophobic portions. Moreover, the term "micelle" is meant to refer to any electrically charged particle built up from polymeric molecules or ions and oils that occurs in particular colloidal electrolytic solutions.

As used in the present specification, and the appended claims, the term "microemulsion" is meant to be understood as a thermodynamically equilibrium colloid system comprising two liquids. Typical microemulsion particle size is 5-150 nm. Microemulsions are normally transparent or slightly bluish because of the very small particle size.

In the following description, for purposes of explanation, numerous specific details are set forth in order to provide a thorough understanding of the present system and method for forming and controllably dispensing a jettable pharmaceutical based microemulsion. It will be apparent, however, to one skilled in the art, that the present method may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Exemplary Structure

Figure 1:
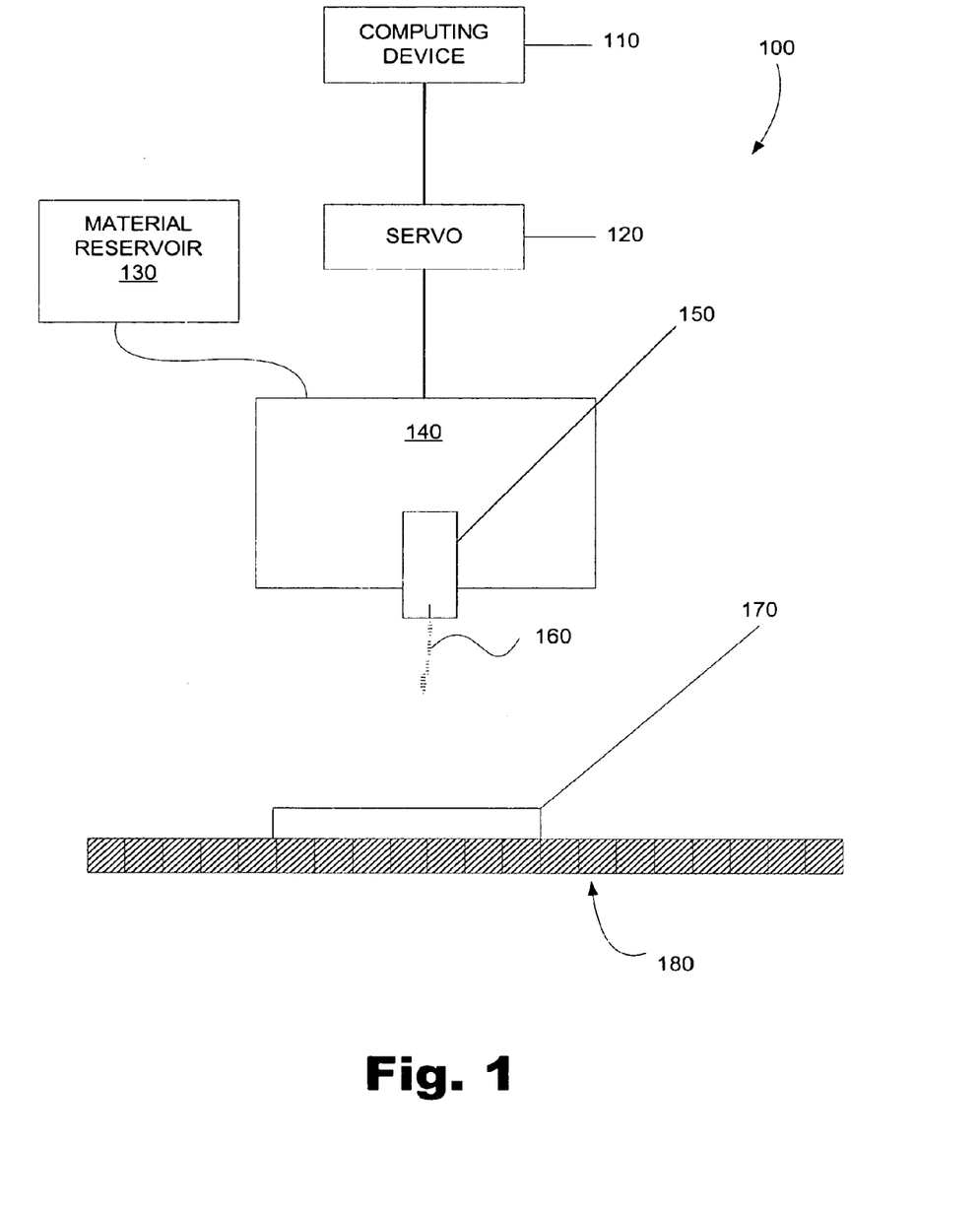
FIG. 1 is a simple block diagram illustrating a system used to deposit a jettable pharmaceutical based microemulsion onto an edible substrate, according to one exemplary embodiment.

FIG. 1 illustrates an exemplary formulation system (100) that may be used to apply a jettable pharmaceutical based microemulsion (160) to an edible structure (170) according to one exemplary embodiment. As shown in FIG. 1, the present system includes a computing device (110) controllably coupled through a servo mechanism (120) to a moveable carriage (140) having an inkjet dispenser (150) disposed thereon. A material reservoir (130) is also illustrated as fluidly coupled to the inkjet material dispenser (150). Moreover, a substrate (180) is located adjacent to the inkjet dispenser (150) having an edible structure (170) disposed thereon. The edible structure (170) is configured to receive a jettable pharmaceutical based microemulsion (160). The above-mentioned components of the present formulation system (100) will now be described in further detail below.

The computing device (110) that is controllably coupled to the servo mechanism (120), as shown in FIG. 1, controls the selective deposition of the jettable pharmaceutical based microemulsion (160) onto the edible structure. According to one exemplary embodiment, a digital representation of the desired deposition of jettable pharmaceutical based microemulsion (160) may be generated on an application hosted by the computing device (110). The generated representation may then be converted into servo instructions that are housed in a processor readable media (not shown). When accessed by the computing device (110), the instructions housed in the processor readable media are used to control the servo mechanisms (120) as well as the movable carriage (140) and the inkjet dispenser (150), causing them to selectively deposit the jettable pharmaceutical based microemulsion (160). The computing device (110) illustrated in FIG. 1 may be, but is in no way limited to, a workstation, a personal computer, a laptop, a personal digital assistant (PDA), or any other processor containing device.

The moveable carriage (140) of the present formulation system (100) illustrated in FIG. 1 is a moveable material dispenser that may include any number of inkjet material dispensers (150) configured to dispense the present jettable pharmaceutical based microemulsion (160). The moveable carriage (140) may be controlled by a computing device (110) and may be controllably moved by, for example, a shaft system, a belt system, a chain system, etc. making up the servo mechanism (120). As the moveable carriage (140) operates, the computing device (110) may inform a user of operating conditions as well as provide the user with a user interface.

As a desired quantity of the jettable pharmaceutical based microemulsion (160) is printed, the computing device (110) may controllably position the moveable carriage (140) and direct one or more of the inkjet dispensers (150) to selectively dispense the jettable pharmaceutical based microemulsion at predetermined locations as digitally addressed drops. The inkjet material dispensers (150) used by the present formulation system (100) may be any type of inkjet dispenser configured to perform the present method including, but in no way limited to, thermally actuated inkjet dispensers, mechanically actuated inkjet dispensers, electro-statically actuated inkjet dispensers, magnetically actuated dispensers, piezo-electrically actuated inkjet dispensers, continuous inkjet dispensers, etc.

The material reservoir (130) that is fluidly coupled to the inkjet material dispenser (150) houses the jettable pharmaceutical based microemulsion (160) prior to printing. The material reservoir (130) may be any sterilizable container configured to hermetically seal the jettable pharmaceutical based microemulsion (160) prior to printing and may be constructed of any number of materials including, but in no way limited to, metals, plastics, composites, ceramics, or appropriate combinations thereof.

FIG. 1 also illustrates the components of the present system that facilitate reception of the jettable pharmaceutical based microemulsion (160) and the edible structure (170). As shown in FIG. 1, a substrate (180) may receive and/or positionally secure an edible structure (170) during a printing operation. The edible structure (170) configured to receive the jettable pharmaceutical based microemulsion (160) may be any number of edible substrates. According to one exemplary embodiment, the edible structure (170) includes, but is in no way limited to, polymeric and/or paper organic film formers. Non-limiting examples of such edible structures include, but are in no way limited to, starch (natural and chemically modified); glycerin based sheets with or without a releasable backing, and the like; proteins such as gelatin, wheat gluten, and the like; cellulose derivatives such as hydroxypropylmethylcellulose, methocel, and the like; other polysaccharides such as pectin, xanthan gum, guar gum, algin, pullulan (an extracellular water-soluble microbial polysaccharide produced by different strains of *Aureobasidium pullulans*), and the like; sorbitol; seaweed; synthetic polymers such as polyvinyl alcohol, polymethylvinylether (PVME), poly-(2-ethyl 2-oxazoline), polyvinylpyrrolidone, and the like. Further examples of edible delivery substrates are those that are based on milk proteins, rice paper, potato wafer sheets, and films made from restructured fruits and vegetables. It should be understood that one or more of the above listed substrate materials, as well as other substrate materials, may be used in combination in some embodiments. The formation and composition of the jettable pharmaceutical based microemulsion (160) will now be described in detail below.

Figure 2:
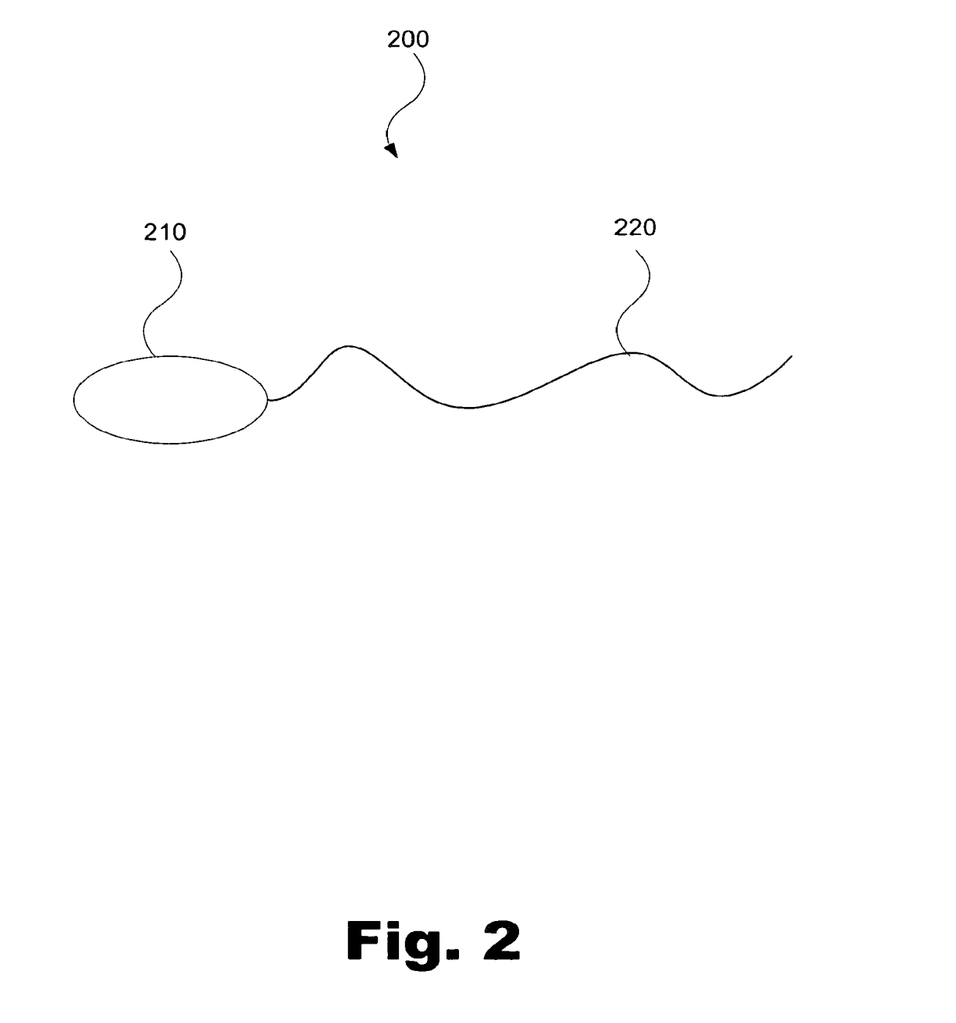
FIG. 2 is a magnified side view illustrating the structure of a surfactant molecule, according to one exemplary embodiment.

According to one exemplary embodiment, the jettable pharmaceutical based microemulsion (160) is made possible by the inclusion of a number of surfactant "amphiphile" or "hydrotrope" molecules (200) similar to that illustrated in FIG. 2. As illustrated in FIG. 2, the exemplary surfactant molecule (200) includes a polar head (210) and a hydrophobic tail (220) typically made of hydrocarbons. The surfactant molecules (200) may be formed as a result of the formation of an interfacial ion-pair formed between an amino acid and a fatty acid. Due to the varying affinity for aqueous solutions exhibited by the surfactant molecules (200), the surfactant molecules facilitate the formation of micelles or bicontinuous phases within the microemulsion as will be described in further detail below with reference to FIGS. 3 and 4.

Figure 3:
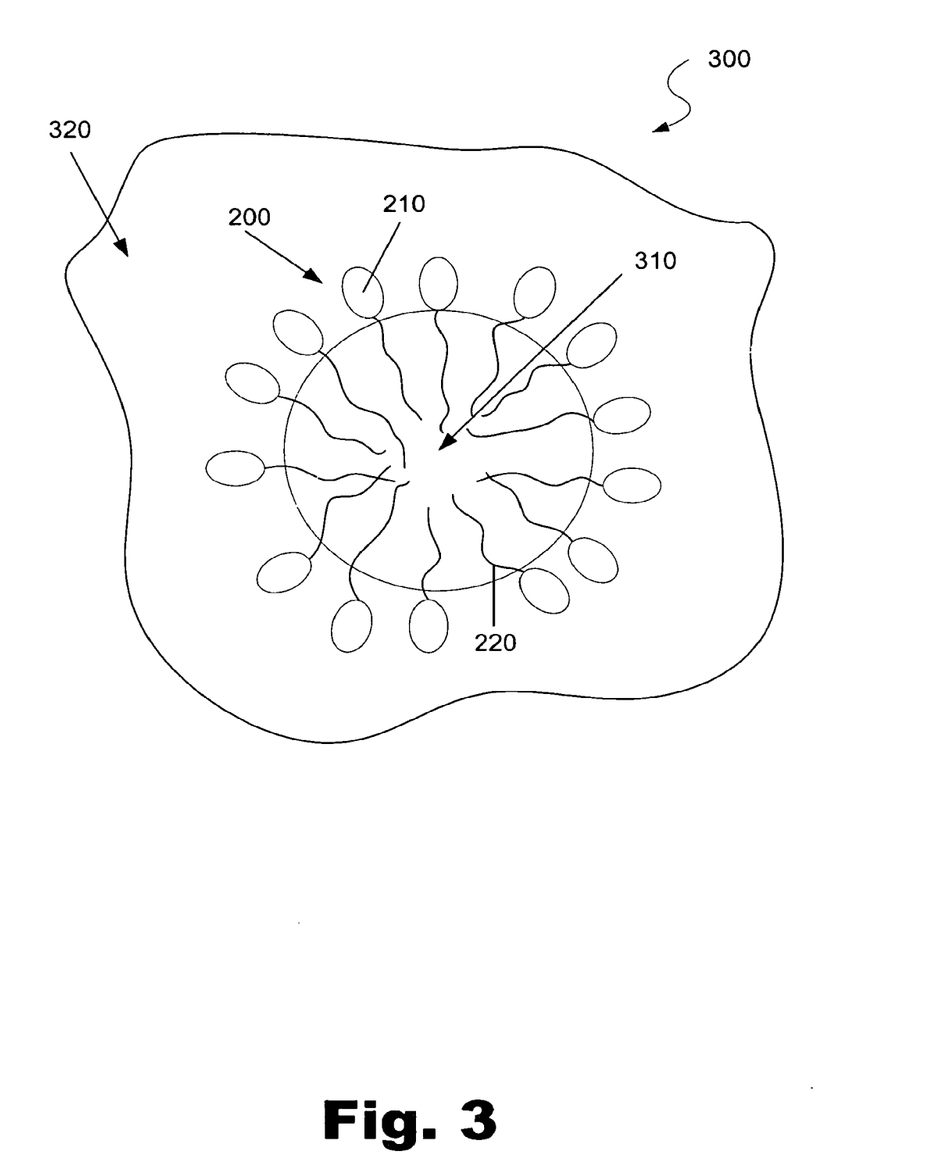
FIG. 3 is a magnified view illustrating an oil-based micelle, according to one exemplary embodiment.

FIG. 3 illustrates an oil-based micelle (300) including a number of surfactant molecules (200), according to one exemplary embodiment. As illustrated in FIG. 3, the surfactant molecules (200), when forming micelles, position themselves at the phase boundary between the oil droplet (310) and the aqueous solution (320). As illustrated in FIG. 3, during the formation of oil-based micelles (300), the hydrophobic tails (220) of the surfactant molecules (200) position themselves away from the aqueous solution (320) into the oil droplet (310) while the hydrophilic polar heads (210) of the surfactant molecules (200) are oriented in the aqueous solution (320). This interaction between the surfactant molecules and the dispersed fluids enables the formation of a microemulsion. According to one exemplary embodiment illustrated in FIG. 3, the oil-based micelle (300) is configured to confine any entrapped or dissolved material until the micelle (300) adheres to the outer membrane of a target cell. Consequently, when the oil-based micelles are applied to a pharmaceutical delivery application, drug efficacy may be increased while overall toxicity is reduced due to the direct delivery of the pharmaceutical to the needed cells.

Figure 4:
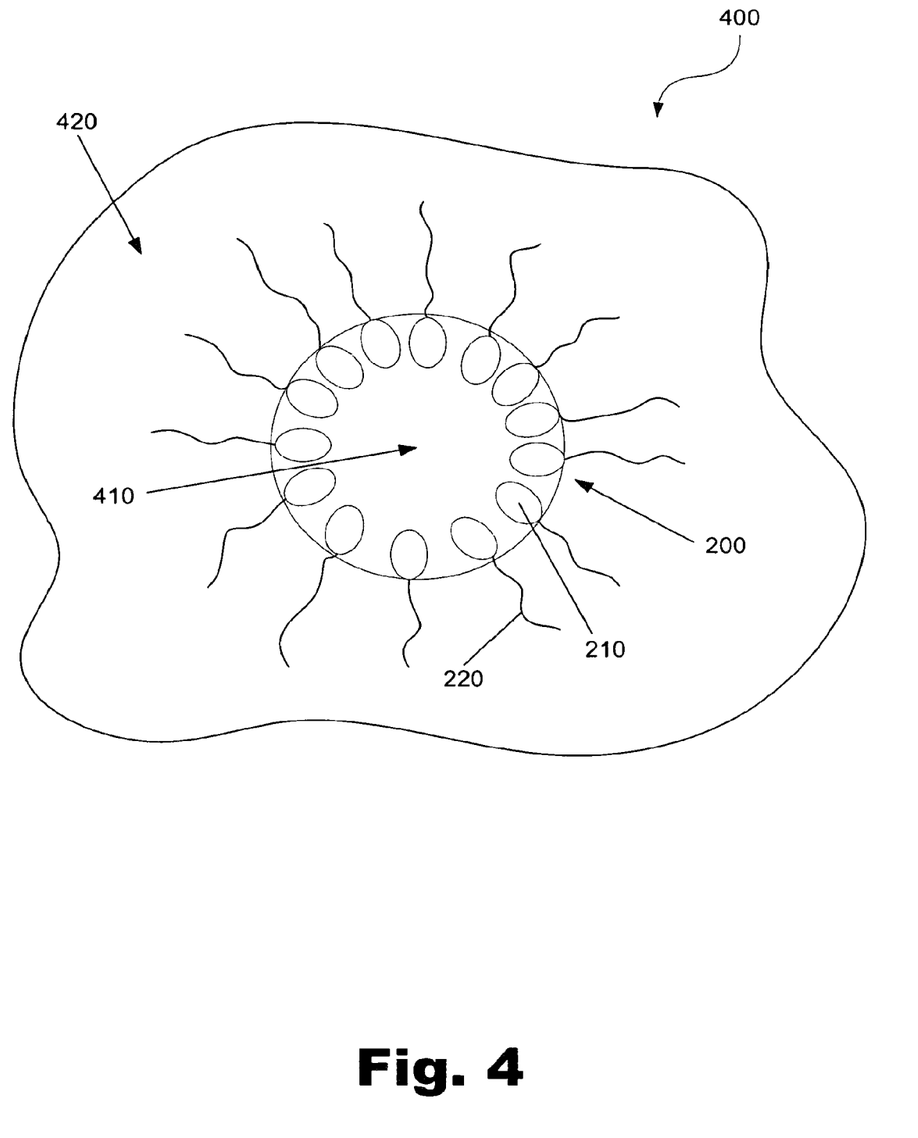
FIG. 4 is a magnified view illustrating a water-based micelle, according to one exemplary embodiment.

In addition, as illustrated in FIG. 4, the ratio of aqueous solution to oil may be varied to form water-based micelles (400) in a water-in-oil type microemulsion. As illustrated in FIG. 4, a number of water-based micelles (400) may be formed out of aqueous droplets (410) containing the polar head portion (210) of the surfactant molecule (200) while the hydrophobic tail portion (220) is extended into the oil solution (420) of the microemulsion. As illustrated above, the pharmaceutical payload may be solubilized within the oil solution (420) and evenly dispensed by an inkjet material dispenser. The exemplary composition of the jettable pharmaceutical based microemulsion (160; FIG. 1) will now be described in further detail below.

Exemplary Composition

According to one exemplary embodiment, the present jettable pharmaceutical based microemulsion (160; FIG. 1) includes an edible surfactant such as a hydrotrope; one of a naturally occurring-pharmaceutical solubilizing oil, an edible oil, and/or an oil that can be subsequently removed by evaporation; and an aqueous solution which may include co-solvents. Exemplary embodiments of the jettable pharmaceutical based microemulsion components, as well as additional additives, are described below.

As noted above, the present jettable pharmaceutical based microemulsion (160; FIG. 1) includes an amphiphile surfactant configured to modify the surface tension of the interface between the aqueous solution and the naturally occurring pharmaceutical solubilizing oil, thereby enabling the formation of the present microemulsion. While those skilled in the art will readily identify a number of edible surfactants, the surfactant may include, but is in no way limited to hydrophobic surfactants such as lecithin, sphingolipids, and galacto lipids, or hydrophilic surfactants such as ethoxylated castor oil; polyoxyl 40 hydrogenated castor oil; ethoxylated fatty esters; sucrose fatty esters; mono-, di-, and trimesters of sorbitol and sorbitan and polyoxyelhylene derivatives thereof; alkyl glucosides or alkyl polyglucosides; ethoxylated monohydroxy stearic acid, bile salts, polyoxyethylene-sorbitan monooleate, polyoxyethylene-sorbitan monopalmitate, polyoxyethylene-sorbitan monolaurate, polyoxyethylene sorbitan monostearate, cholic acid or bile salts, nicotinic acid and nicotinamide derivatives, acetylininc alcohols, polyhydroxylated alcohols, aromatic sulfonate salts such as xylene sulfonates, naphthalene sulfonates, cymene sulfonate, Ethylene Oxide-Propylene Oxide block (pluronic) polymers, and appropriate mixtures thereof. Additionally, the surfactants may be formed due to an ion-pair formation between any edible yet basic amino acid including, but in no way limited to, L-arginine and L-lysine and a fatty acid including, but in no way limited to, stearic acid and oleic acid. According to this exemplary embodiment, the emulsions may be formed as the amino acid groups of the amino acids react with the carboxylic acid group of the fatty acids to form an interfacial ion-pair. The amino acids and the fatty acids may be present in the aqueous solution or naturally occurring pharmaceutical solubilizing oil as illustrated below. According to one exemplary embodiment, the surfactant comprises up to 15% by weight of the total microemulsion.

Additionally, the present system and method may be formed using a number of naturally occurring pharmaceutical solubilizing oils, edible silicone oils or removable oils. While there are several edible, environmentally benign, non toxic, non corrosive, biodegradable, and FDA approved oils available for pharmaceutical use, the incorporation of naturally occurring pharmaceutical solubilizing oils ensures that the resulting jettable pharmaceutical based microemulsion is edible and contains ingredients approved by the FDA. According to one exemplary embodiment, the present naturally occurring pharmaceutical solubilizing oils may include, but are in no way limited to, castor oil, oleic acid and oleyl alcohol, coconut oil, mineral oil, cottonseed oil, squalene, safflower oil, and fatty esters such as triolein (glyceryl trioleate) and ethyl oleate. According to another exemplary embodiment, the oils are removable oils that can be evaporated under the influence of heat or vacuum after the precision dosing process. Examples of such oils are aliphatic alcohols such as pentanol, butanol, and hexanol; cyclic alcohols such as cyclopentanol and 4-methyl cyclohexanol; terpenes such as hydroxycitronellal, alpha-terpeniol and eugenol; aromatic side chain alcohols such as cinnamoyl alcohol and benzyl alcohol; ketones such as cyclopentanone and cyclohexanone; and esters such as diethyl malonate.

The aqueous solution that forms the vehicle portion of the jettable pharmaceutical based microemulsion may include, but is in no way limited to, water and a solvent or amino acid. The aqueous vehicle component of the present system and method is included in the present jettable pharmaceutical based microemulsion (160; FIG. 1) for stable dispersion and transport of the pharmaceutical payload component contained within the micelle forming component as well as any other additives. The aqueous vehicle imparts a jettable viscosity to the jettable pharmaceutical based microemulsion (160; FIG. 1) while evaporating at a rate sufficient to make a dispensed dosage resistant to smudging soon after it is deposited. Additionally, as noted previously, the aqueous vehicle component may or may not include a solvent. According to one exemplary embodiment, the aqueous vehicle comprises water. In addition to having a low cost, water is effective as a solvent for many additives, greatly reduces inkjet dispenser compatibility issues, effectively suspends oral drug formulations and colorants, and effectively controls drying rates of the aqueous vesicle pharmaceutical. In another exemplary embodiment, the aqueous vehicle component of the present jettable pharmaceutical based microemulsion (160; FIG. 1) includes a mixture of water and an edible solvent, amino acid, or fatty acid such as salts, stearic acid, oleic acid, L-arginine, L-lysine, etc.

The pharmaceutical payload component of the present jettable pharmaceutical based microemulsion (160; FIG. 1) is a finely ground pharmaceutical particle receptive to solubilization by an edible and naturally occurring oil. According to one exemplary embodiment, the pharmaceutical payload component is pre-processed to a size of less than 1 micron average dimensions to aid in its dissolution into the present microemulsion. Additionally, the pharmaceutical payload component may take the form of any number of immiscible and non-immiscible pharmaceutical products including, but in no way limited to, water insoluble peptides, antimicrobials, proton pump inhibitors, calcium channel blockers, beta blockers, anesthetics, steroids, antioxidants, rennin inhibitors, alkaloids, cytostaticas, anti-coagulants, lipid regulating agents, anti-depressants, neuroleptics, immunosuppressants, immunomodulators, antibiotics, anti-inflammatory agents, antineoplastics, paclitaxel, taxol, tyloxapol, docetaxel, lovastatin, indometacine, diclofenac, naproxen, dexibuprofen, rofecoxib, celecoxib, celecoxib nitrendipine, flurbiprofen, diclofenac, ketoprofen, piroxicam, tenoxicam, vincristine, vinblastine, insulin, calcitonin, erythropoietin, cephalosporin, desmopressin, taxol, etoposide, leuprolide, cyclosporins such as cyclosporin A, dihydrocyclosporin C, dihydrocyclosporin D, cyclosporin D, and/or derivatives thereof.

In addition to the above-mentioned components of the present jettable pharmaceutical based microemulsion (160; FIG. 1), a number of additives may be employed to optimize the properties of the ink composition for specific applications. For example, as is well-known to those skilled in the art, biocides may be used in the ink composition to inhibit growth of microorganisms. Other known additives such as viscosity modifiers, humectants, antifoaming agents, surface tension adjusting agents, rheology adjusting agents, pH adjusting agents, drying agents, colors, and other acrylic or non-acrylic polymers may be added to improve various properties of the ink compositions as desired.

As noted previously, the present system and method may be used to vary the release rate of the desired pharmaceutical product. According to the present exemplary system and method, the release rate determining factor for the absorption of the desired pharmaceutical product in the pharmaceutical based microemulsion is not the enzymatic metabolism of triglycerides, rather the determining factor rests primarily in the breakdown of the naturally occurring oil globules into microparticles since the enzymes acting on the pharmaceutical based microemulsion act mainly at the surface of the oil globules. Consequently, the release rate of the pharmaceutical product may be selectively adjusted by varying the naturally occurring oil used.

According to one exemplary formulation, a pharmaceutical based microemulsion was formed by combining L-arginine (5%), stearic acid (6%), and soy bean oil (15%) in an aqueous solution. After formulation, an observation and subsequent testing was performed illustrating that the above-mentioned combination forms very stable microemulsions that manifest excellent ink-jet material dispenser jetting characteristics.

While a number of exemplary formulations and ingredients for the present jettable pharmaceutical based microemulsion are given above, they are in no way meant to limit the present system. Rather, they are presented for exemplary purposes only.

Exemplary Implementation and Operation

Figure 5:
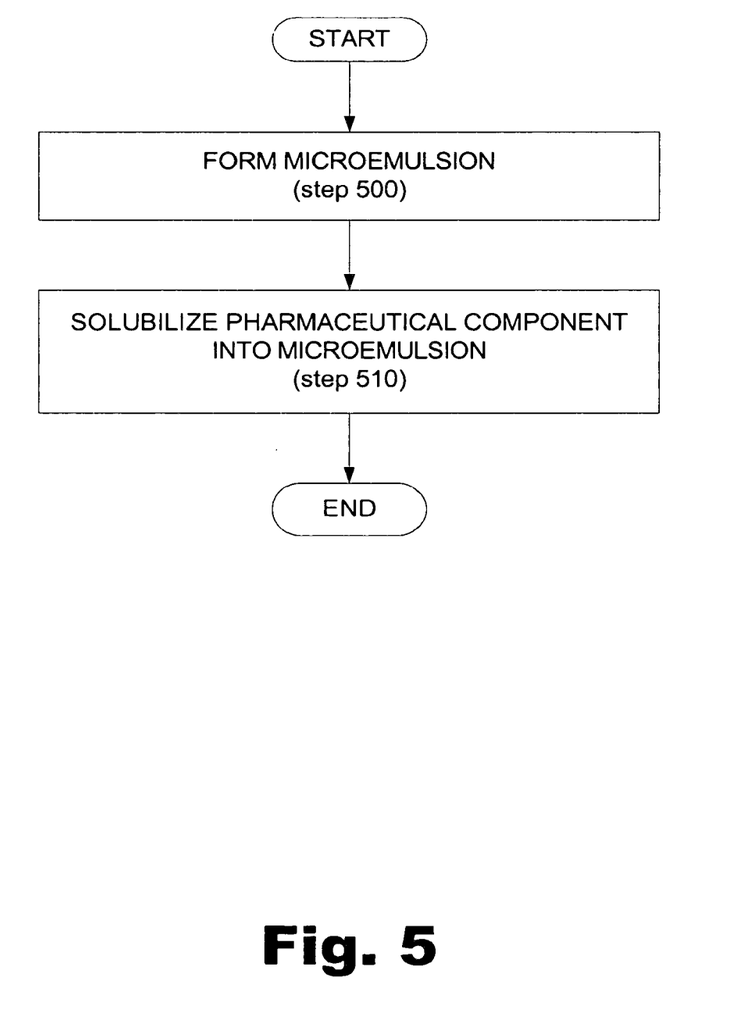
FIG. 5 is a flow chart illustrating a method for forming a jettable pharmaceutical based microemulsion, according to one exemplary embodiment.

FIG. 5 illustrates an exemplary method for the formation of the jettable pharmaceutical based microemulsion (160; FIG. 1) according to one exemplary embodiment. As illustrated in FIG. 5, the formation method begins by preparing a microemulsion (step 500). Once the microemulsion is prepared, a desired pharmaceutical component is solubilized into the formed microemulsion (step 510). Each of the above-mentioned steps will now be explained in further detail below.

As shown in FIG. 5, the present formation method begins by preparing a desired microemulsion (step 500). According to one exemplary embodiment, the desired microemulsion may be prepared by combining the naturally occurring, edible, or removable pharmaceutical solubilizing oil, the edible surfactant, and the aqueous solution, as well as any additional additives, as discussed above. Once the materials are combined into an aqueous solution, the hydrophobic groups (the naturally occurring pharmaceutical solubilizing oil and the hydrophobic tails of the surfactant molecules) self-associate and form one or more micelles in the aqueous solution. While slight agitation and/or heat may be introduced to the mixture to further facilitate the formation of the micelles, it is not required. Rather, because microemulsions are thermodynamically equilibrium systems, they form spontaneously, requiring little or no mechanical work in their formation.

Once the desired microemulsion is prepared, a desired pharmaceutical product may be solubilized into the microemulsion (step 510). Again, a mere combination of the microemulsion and the desired pharmaceutical product will self-associate into the desired micelles. According to this exemplary embodiment, due to the insolubility of the desired pharmaceutical in water, it will equilibrate over a period of time into the oil droplet (310; FIG. 3) portion of the microemulsion.

Alternatively, the jettable pharmaceutical based microemulsion may be formed by first dissolving the desired pharmaceutical product into the naturally occurring-pharmaceutical solubilizing oil to form an oil-in-water microemulsion. According to this exemplary embodiment, the desired pharmaceutical product is dissolved in the naturally occurring pharmaceutical solubilizing oil until a transparent or semi-transparent liquid results. Dissolution of the desired pharmaceutical product may be facilitated by the use of slight agitation and/or thermal energy and rolling in a container over a roller mill to cause through mixing. Complete dissolution of the desired pharmaceutical product may then be confirmed by microscopy.

After the desired pharmaceutical product has been completely dissolved in the naturally occurring pharmaceutical solubilizing oil, the edible surfactant and the aqueous solution may be added with slight agitation to form the desired jettable pharmaceutical based microemulsion. According to this exemplary embodiment, the desired pharmaceutical product remains in solution in the naturally occurring pharmaceutical solubilizing oil during the production of the microemulsion. Consequently, the naturally occurring-pharmaceutical solubilizing oil and the dissolved pharmaceutical product are distributed throughout the aqueous phase of the microemulsion as very tiny particles that may then be readily taken up by the human body.

Once the jettable pharmaceutical based microemulsion has been satisfactorily formed, it will exhibit a number of desirable properties. According to one exemplary embodiment, the jettable pharmaceutical based microemulsion will be suitable for inkjet printing from an inkjet material dispenser (150; FIG. 1). According to this exemplary embodiment, the resulting pharmaceutical based microemulsion has a viscosity that is no more than approximately 5 centipoise, under the operating temperature and conditions, although the value may be outside of this range. In addition, the surface tension of the final microemulsion is typically between about 25 to about 60 dynes per centimeter.

Figure 6:
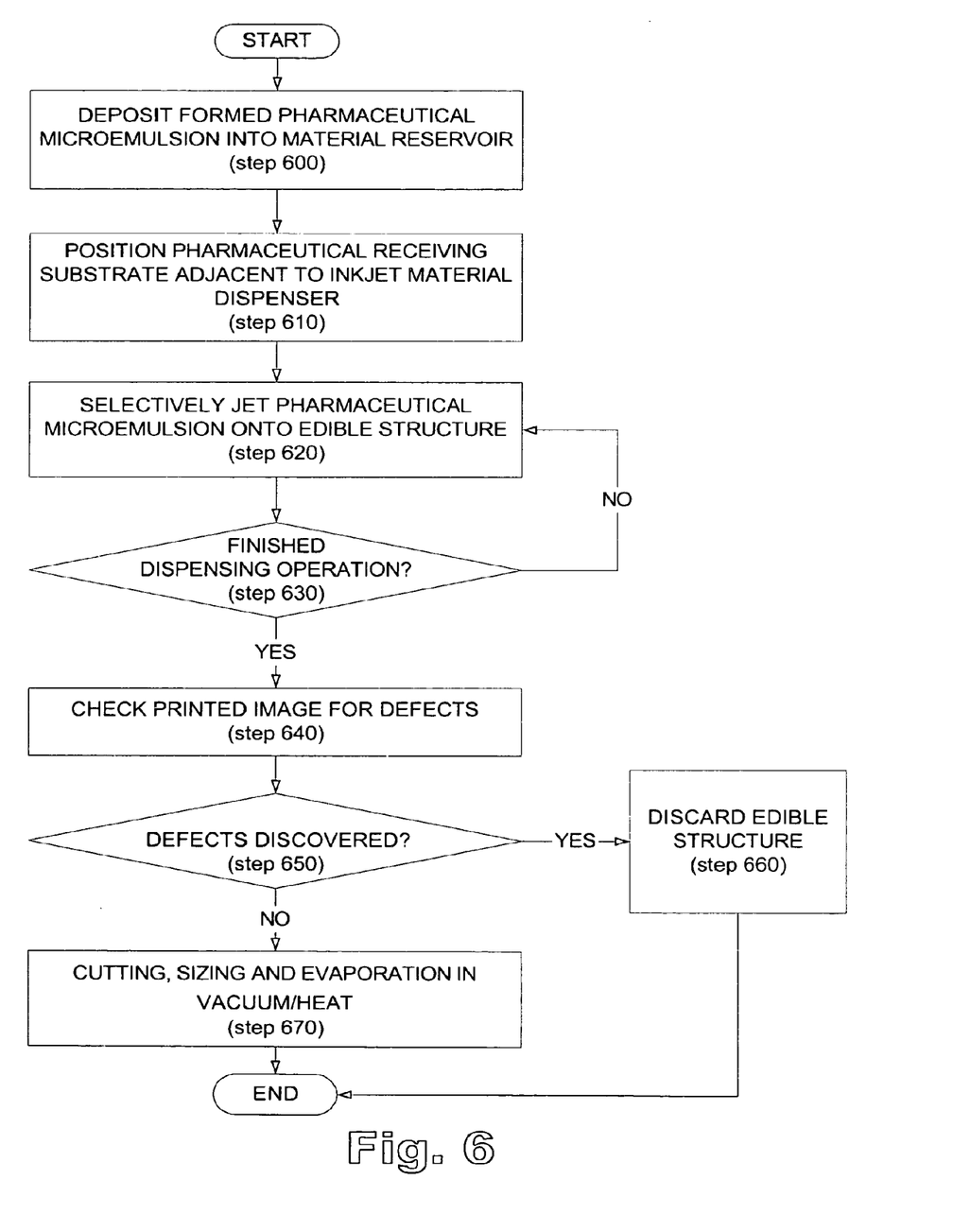
FIG. 6 is a simple block diagram illustrating a method for dispensing a jettable pharmaceutical based microemulsion, according to one exemplary embodiment.

Once the above-mentioned jettable pharmaceutical based microemulsion (160; FIG. 1) is formed, it may be selectively jetted onto an edible structure (170; FIG. 1) or other substrate to form a solid drug dosage, to prepare a drug dosage designed for combination therapy, or in a gradient structure to form both high and low load zones in certain sub areas of the edible structure. FIG. 6 illustrates an exemplary method for selectively jetting a pharmaceutical based microemulsion onto an edible structure to specific areas and shapes image-wise corresponding to the desired dosage shape according to one exemplary embodiment. As shown in FIG. 6, the present method begins by depositing the formed pharmaceutical based microemulsion into the material reservoir of a formulation system (step 600). Once the pharmaceutical based microemulsion is deposited, an edible structure (170; FIG. 1) is positioned adjacent to the inkjet material dispenser (150; FIG. 1) of the present formulation system (step 610). When positioned, the inkjet material dispenser (150; FIG. 1) selectively deposits the jettable pharmaceutical based microemulsion (160; FIG. 1) onto the edible structure (step 620). Upon deposition of the jettable pharmaceutical based microemulsion onto the edible structure, a determination is made as to whether the present formulation system (100; FIG. 1) has completed its formulation dispensing operation (step 630). If it is determined that the pharmaceutical formulation dispensing is not complete (NO, step 630), the formulation system again selectively jets a jettable pharmaceutical based microemulsion onto the edible structure (step 620). If, however, the pharmaceutical dispensing operation is complete (YES, step 630), the printed media is optionally examined for defects (step 640). If no defects are found (NO, step 450), the jettable pharmaceutical based microemulsion dispensing process is complete. In subsequent steps, the media may be processed by dicing, slicing and treating to heat or vacuum and packaging (step 670). If, however, printing defects are found on the printed media (YES, step 650), the edible structure may be discarded (step 660) or otherwise re-processed. The above-mentioned steps will now be described in further detail below.

As shown in FIG. 6, the present method for printing a jettable pharmaceutical based microemulsion on an edible structure begins by depositing the formed jettable pharmaceutical based microemulsion into a material reservoir (step 600). The deposition of the jettable pharmaceutical based microemulsion into a material reservoir may be performed by a user or alternatively by a fluid channeling system disposed between a jettable pharmaceutical based microemulsion forming apparatus and the formulation system (100; FIG. 1).

After the formed jettable pharmaceutical based microemulsion is deposited into a material reservoir (step 600), an edible structure is positioned adjacent to the inkjet material dispenser (150; FIG. 1) of the present formulation system (step 610). As shown in FIG. 1, the edible structure (170) may be positioned under the formulation system (100) by a moveable substrate (180). Alternatively, an operator or a number of mechanical transportation apparatuses may manually place the edible structure (170) adjacent to the formulation system (100).

Once the edible structure (170) is correctly positioned, the present formulation system (100) may be directed by the computing device (110) to selectively jet the jettable pharmaceutical based microemulsion (160) onto the edible structure (step 620; FIG. 6). As was mentioned previously, the desired dosage of the jettable pharmaceutical based microemulsion to be printed on the edible structure (170) may initially be determined on a program hosted by the computing device (110). The program created dosage may then be converted into a number of processor accessible commands, which when accessed, may control the servo mechanisms (120) and the movable carriage (140), causing them to selectively emit a specified quantity of jettable pharmaceutical based microemulsion (160) onto the edible structure (170).

The precise metering capability of the inkjet material dispenser (150) along with the ability to selectively emit the metered quantity of aqueous vesicle pharmaceutical (160) onto precise, digitally addressed locations makes the present system and method well suited for a number of pharmaceutical delivery applications. According to one exemplary embodiment, the precision and addressable dispensing provided by the present inkjet material dispenser (150) allows for one or more compositions to be dispensed on a single edible structure (170). According to this exemplary embodiment, a combination therapy may be produced in a customized dosage for a patient. Combination therapy is to be understood as any dosage including two or more pharmaceutical products combined to achieve desired results. According to another exemplary embodiment certain regions of the dosage may be printed with a gradient to allow for an initial high concentration "burst" and a low concentration slow release zone. This gradient deposition will vary both the concentration and temporal release rate of the dispensed pharmaceutical. Precision of the resulting oral drug deposition may be varied by adjusting a number of factors including, but in no way limited to, the type of inkjet material dispenser (150) used, the distance between the inkjet material dispenser (150) and the edible structure (170), and the dispensing rate. Once the jettable pharmaceutical based microemulsion (160) has been selectively deposited onto the edible structure (170), according to the desired dosage, the deposited jettable pharmaceutical based microemulsion may be absorbed by the edible structure or remain in a fixed state on top of the edible structure. Consequently, the jettable pharmaceutical based microemulsion is affixed to the edible structure until consumption initiates a selective release thereof.

Upon deposition of the aqueous vesicle pharmaceutical, it is determined whether or not the jettable pharmaceutical based microemulsion dispensing operation has been completed on the edible structure (step 630; FIG. 6). Completion of the jettable pharmaceutical based microemulsion dispensing operation may be evaluated by a system operator or by the coupled computing device (110). According to one exemplary embodiment, the computing device (110) determines whether sufficient jettable pharmaceutical based microemulsion (160) has been dispensed to produce the desired dosage on the edible structure (170). If sufficient jettable pharmaceutical based microemulsion (160) has not been dispensed (NO, step 630; FIG. 6), the formulation system (100) continues to selectively deposit jetted pharmaceutical based microemulsion onto the edible structure (step 620; FIG. 6). If, however, sufficient jettable pharmaceutical based microemulsion (160) has been dispensed (YES, Step 630; FIG. 6), the dispensed quantity may optionally be checked for defects (step 640; FIG. 6).

In order to check the printed media for defects (step 640; FIG. 6), according to one exemplary embodiment, the edible structure (170) or other image receiving substrate may be analyzed according to weight, volume, or optical properties for obvious defects that may make the resulting substrate unacceptable. According to one exemplary embodiment, the edible structure (170) is subject to a series of optical scans configured to detect any alignment or deposition defects. Additionally, adequacy of the volume of jettable pharmaceutical based microemulsion (160) dispensed onto an edible structure (170) may be evaluated by a number of flow-rate sensors (not shown) disposed on the inkjet material dispenser (150).

According to one exemplary embodiment, if defects are discovered on the edible structure (YES, step 650; FIG. 6), the edible structure may be discarded (step 660; FIG. 6) and the system adjusted. If, however, no image defects are discovered (NO, step 650; FIG. 6) the edible structure (270) may be packaged or otherwise distributed. Distribution of the edible structure includes applying the proper coating, cutting, sizing, and/or packaging the edible structure (step 670; FIG. 6).

According to one exemplary embodiment, the above-mentioned system and method may be performed on a large edible structure that is then sliced or otherwise divided into smaller individual dosages. Additionally, evaporation processes, such as thermal or vacuum treatments, may be performed on the edible structure to remove an oil according to one exemplary embodiment.

In conclusion, the present system and method for producing and dispensing a jettable pharmaceutical based microemulsion allows for precision dispensing of insoluble or low-solubility pharmaceuticals. More specifically, the insoluble or low-solubility pharmaceuticals are solubilized into a jettable microemulsion based on naturally occurring oils such as soybean oil. The system consists of aqueous microemulsions, with or without a co-solvent and a "pay load" pharmaceutical agent. Moreover, the use of an inkjet material dispenser allows a high precision of dosage forms. In addition, the jettable pharmaceutical based microemulsions exhibit a number of desirable properties such as excellent jettability, stability, uniform drop formation, fine particle size, ability to form individual, gel-drops of nanometer size, and precise control over the dosage amount. Additionally, the systems and methods disclosed are cost effective when compared to traditional formulation methods while being able to precisely deliver and prepare custom dosages without special treatments, modifications, or use of special equipment.

The preceding description has been presented only to illustrate and describe exemplary embodiments of the present system and method. It is not intended to be exhaustive or to limit the system and method to any precise form disclosed. Many modifications and variations are possible in light of the above teaching. It is intended that the scope of the system and method be defined by the following claims.

What is claimed is:

1. A method for dispensing an oral medication comprising:
    selectively dispensing a microemulsion comprising a water insoluble pharmaceutical in a gradient amount with an inkjet material dispenser onto an edible substrate;
    in which the dispensed pharmaceutical is initially released into a patient at a relatively higher concentration and decreasingly released into a patient at a relatively lower concentration thereafter.

2. The method of claim 1, further comprising preparing the microemulsion by forming a combination of an oil, an edible surfactant, and an aqueous solution;
    in which the oil comprises one of a naturally occurring pharmaceutical solubilizing oil or a removable oil; and
    the combination resulting in a formation of a plurality of micelles emulsified in a solution.

3. The method of claim 2, in which preparing the microemulsion further comprises one of agitating the combination or adding thermal energy to the combination.

4. The method of claim 2, in which the oil comprises one of a castor oil, an oleic acid and an oleyl alcohol, a coconut oil, a mineral oil, a cottonseed oil, a squalene, a safflower oil, or a fatty ester.

5. The method of claim 1, in which the pharmaceutical comprises one of a water insoluble peptide, an antimicrobial, a proton pump inhibitor, a calcium channel blocker, a beta blocker, an anesthetic, a steroid, an antioxidant, a rennin inhibitor, an alkaloid, a cytostatica, an anti-coagulant, a lipid regulating agent, an anti-depressant, a neuroleptic, an immunosuppressant, an immunomodulator, an antibiotic, an anti-inflammatory agent, an antineoplastic, a paclitaxel, a taxol, a tyloxapol, a docetaxel, a lovastatin, an indometacine, a diclofenac, a naproxen, a dexibuprofen, a rofecoxib, a celecoxib, a celecoxib nitrendipine, a flurbiprofen, a diclofenac, a ketoprofen, a piroxicam, a tenoxicam, a vincristine, a vinblastine, an insulin, a calcitonin, an erythropoietin, a cephalosporin, a desmopressin, an etoposide, a leuprolide, or a cyclosporin.

6. The method of claim 2, in which the edible surfactant comprises one of a lecithin, a sphingolipid, a galacto lipid, an ethoxylated castor oil, a polyoxyl 40 hydrogenated castor oil, an ethoxylated fatty ester, a sucrose fatty ester, a sorbitol, a sorbitan, a polyoxyethylene derivative, an alkyl glucoside, an alkyl polyglucoside, an ethoxylated mono-hydroxy stearic acid, a bile salt, a polyoxyethylene-sorbitan monooleate, a polyoxyethylene-sorbitan monopalmitate, a polyoxyethylene-sorbitan monolaurate, a polyoxyethylene sorbitan monostearate, cholic acid, nicotinic acid and nicotinamide derivatives, acetylininc alcohols, polyhydroxylated alcohols, or aromatic sulfonate salts.

7. The method of claim 2, in which the edible surfactant comprises an ion-pair formation between an amino acid and a fatty acid.

8. The method of claim 7, in which:
    the amino acid comprises one of an L-arginine or an L-lysine; and
    the fatty acid comprises one of a stearic acid or an oleic acid.

9. The method of claim 5, in which the cyclosporin comprises one of cyclosporin A, dihydrocyclosporin C, dihydrocyclosporin D, cyclosporin D.

10. The method of claim 6, in which the aromatic sulfonate salts comprise one of a xylene sulfonate, naphthalene sulfonate, cymene sulfonate, or Ethylene Oxide-Propylene Oxide block (pluronic) polymers.

* * * * *

UNITED STATES PATENT AND TRADEMARK OFFICE
CERTIFICATE OF CORRECTION

PATENT NO. : 8,474,954 B2
APPLICATION NO. : 13/037101
DATED : July 2, 2013
INVENTOR(S) : Makarand Gore Page 1 of 1

It is certified that error appears in the above-identified patent and that said Letters Patent is hereby corrected as shown below:

In he Claims

In column 12, line 33, in Claim 6, delete "acetylininc" and insert -- acetylenic --, therefor.

Signed and Sealed this
Fifth Day of November, 2013

Teresa Stanek Rea
*Deputy Director of the United States Patent and Trademark Office*